US00PP16288P2

(12) United States Plant Patent
Guillen

(10) Patent No.: US PP16,288 P2
(45) Date of Patent: Feb. 21, 2006

(54) **INTERSPECIFIC *IMPATIENS* PLANT NAMED 'BALFAFBLUS'**

(50) Latin Name: *Impatiens hybrida*
Varietal Denomination: Balfafblus

(75) Inventor: Mario Guillen, Cartago (CR)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 11/011,793

(22) Filed: Dec. 13, 2004

(51) Int. Cl.
*A01H 5/00* (2006.01)

(52) U.S. Cl. ..... Plt./317
(58) Field of Classification Search ..... Plt./317
See application file for complete search history.

*Primary Examiner*—Anne Marie Grunberg
*Assistant Examiner*—Annette H Para
(74) *Attorney, Agent, or Firm*—Wood, Phillips, Katz, Clark & Mortimer

(57) ABSTRACT

A new and distinct *Impatiens* plant named 'Balfafblus' characterized by its single, very pale violet-colored flowers, dark green-colored foliage, good basal branching character, and vigorous, mounded and trailing growth habit.

1 Drawing Sheet

Latin name of genus and species of plant claimed: *Impatiens hybrida.*
Variety denomination: 'Balfafblus'.

BACKGROUND OF THE INVENTION

The present invention relates to a new and distinct cultivar of *Impatiens* plant botanically known as *Impatiens hybrida* and hereinafter referred to by the cultivar name 'Balfafblus'.

The new cultivar originated in a controlled breeding program during July 1998 at Cartago, Costa Rica, Central America. The objective of the breeding program was the development of new *Impatiens* cultivars with numerous single flowers, excellent basal branching, and mounded, trailing growth habit.

The female (seed) parent of the new cultivar was the proprietary *Impatiens flaccida* selection designated N510, not patented, characterized by its lilac-colored flowers and mounded, loose habit. The male (pollen) parent of the new cultivar was a pool of pollen from Java Series F1 hybrids, not patented, characterized by medium to large flowers and medium vigor. The new cultivar was discovered and selected by the inventor as a single flowering plant within the progeny of the stated cross-pollination during October 1998 at Cartago, Costa Rica, Central Amercia.

Asexual reproduction of the new cultivar by terminal stem cuttings since October 1998 at Cartago, Costa Rica and West Chicago, Ill., has demonstrated that the new cultivar reproduces true to type with all characteristics, as herein described, firmly fixed and retained through successive generations of such asexual propagation.

SUMMARY OF THE INVENTION

The following characteristics of the new cultivar have been repeatedly observed and can be used to distinguish 'Balfafblus' as a new and distinct cultivar of *Impatiens* plant:

1. Single, very pale violet-colored flowers.
2. Dark green-colored foliage.
3. Good basal branching character.
4. Vigorous, mounded and trailing growth habit.

Plants of the new cultivar differ from plants of the female parent primarily in flower color and from the male parent primarily in flower size and plant vigor.

Of the many commercially available *Impatiens* cultivars known to the inventor, the most similar to the new cultivar is the variety 'Balfaflav', not patented. However, in side-by-side comparisons conducted at West Chicago, Ill., plants of the new cultivar differed from plants of 'Balfaflav' in the following characteristics:

1. Plants of the new cultivar have smaller flowers than plants of 'Balfaflav'.
2. Plants of the new cultivar have smaller leaves than plants of 'Balfaflav'.
3. The flowers of the new cultivar are lighter in color than the flowers of 'Balfaflav'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describe the colors of 'Balfafblus'. The plants were grown in 10 cm pots for 8 weeks in a greenhouse at West Chicago, Ill.

DETAILED BOTANICAL DESCRIPTION

Figure 1:
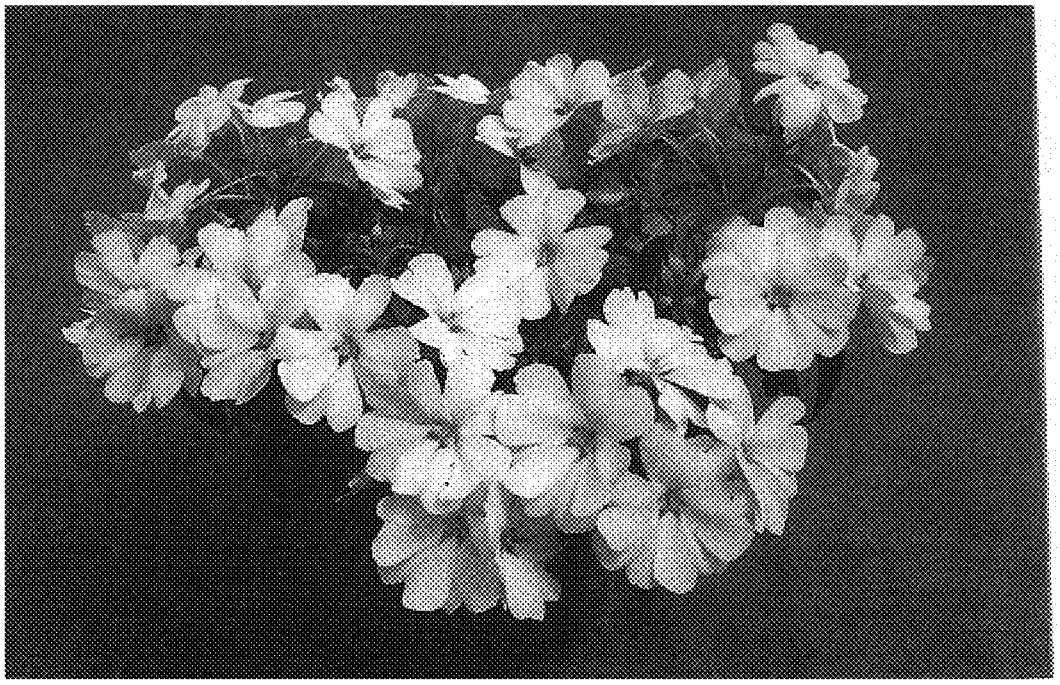
FIG. 1 illustrates a side view of the overall growth and flowering habit of 'Balfafblus'.
Figure 2:
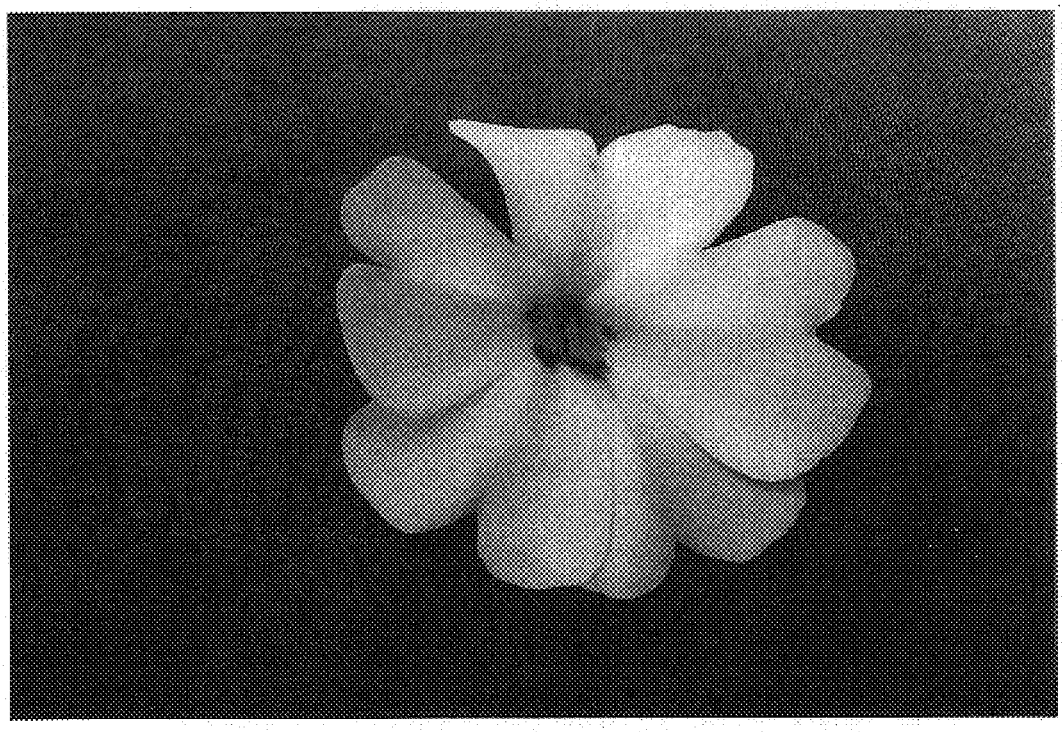
FIG. 2 illustrates a close-up view of an individual flower of 'Balfafblus'.

The new cultivar has not been observed under all possible environmental conditions to date. Accordingly, it is possible that the phenotype may vary somewhat with variations in the environment, such as temperature, light intensity, and day length without, however, any variance in phenotype.

The chart used in the identification of colors described herein is The R.H.S. Colour Chart of The Royal Horticultural Society, London, England, 2001 edition, except where general color terms of ordinary significance are used. The color values were determined on Jul. 20, 2004 between 10:00 and 11:45 a.m. under natural light conditions.

The following descriptions and measurements describe plants produced from cuttings taken from stock plants and grown in a double polycarbonate-covered greenhouse under conditions comparable to those used in commercial practice. The plants were grown at West Chicago, Ill. in 10 cm pots for 8 weeks using a soil-less growth medium. Greenhouse temperatures were maintained at approximately 65°–75° F. during the day and approximately 55°–62° F. during the night. Greenhouse light levels were maintained at approximately 4,000–6,000 footcandles during the day.

Botanical classification: *Impatiens hybrida* cultivar Balfafblus.

Parentage:

*Female (seed) parent.*—Proprietary *Impatiens flaccida* selection designated N510, not patented.

*Male (pollen) parent.*—Pollen pool derived from *Impatiens hawkeri* Java Series F1 hybrids, not patented.

Propagation:

*Type cutting.*—Terminal stem.

*Time to initiate roots.*—Approximately 7–14 days.

*Time to produce a rooted cutting.*—Approximately 21 days.

*Root description.*—Fine, fibrous.

*Rooting habit.*—Freely branching.

Plant description:

*Crop time.*—Approximately 6–8 weeks from planting of rooted cutting to finish.

*Growth habit.*—Compact with good basal branching.

*Form.*—Mounded, trailing.

*Size.*—Height: Approximately 16.5 cm. Width (area of plant spread): Approximately 37.4 cm.

*Branch.*—Quantity: Approximately 3 per plant. Strength: Strong. Length: Approximately 16.5 cm. Diameter: Approximately 5.8 mm. Texture: Glabrous. Color: 146B. Internode length: Approximately 2.4 cm.

*Foliage.*—Quantity per branch: Approximately 20. Fragrance: None. Type: Simple. Arrangement: Opposite. Aspect: At right angle to stem. Shape: Elliptic. Apex: Acuminate. Base: Attenuate: Margin: Serrate/ciliate. Venation pattern: Pinnate, arcuate. Length of mature foliage: Approximately 5.4 cm. Width of mature foliage: Approximately 2.1 cm. Texture of both surfaces: Glabrous. Color of upper surface of mature foliage: 137A, with veins and mid-vein of 145B. Color of lower surface of mature foliage: Closest to 138B with veins and mid-vein of 145B. Petiole length: Approximately 5. mm. Petiole diameter: Approximately 2.5 mm. Petiole texture: Both surfaces are glabrous. Petiole color: 145B.

Flowering description:

*Flowering habit.*—Freely flowering under outdoor growing conditions with substantially continuous blooming from spring through autumn and year round in greenhouse environment.

*Time to first flower.*—Approximately 8 weeks after planting of rooted cutting.

*Lastingness of individual bloom.*—Approximately 5–7 days.

*Quantity of flowers.*—Approximately 44 flowers and 12 buds per plant at any one time.

Flower description:

*Flower bud rate of opening.*—Generally it takes from 3–5 days for buds to progress from first color to fully open flowers.

*Mature flower buds (just before opening).*—Shape: Ovate. Length: Approximately 1.5 cm. Diameter: Approximately 7 mm. Color: 73D.

*Flower description.*—Type: Single. Fragrance: None. Shape: Round. Diameter: Approximately 3.9 cm. Depth: Approximately 1.6 cm. Borne: Above foliage facing upward or outward. Flowers are not persistent or fragrant.

*Petals.*—Quantity per flower: 5. Shape: Obovate. Margin: Entire. Apex: Emarginate. Base of upper petal: Truncate. Base of lateral and lower petals: Attenuate. Texture of both surfaces: Glabrous. Appearance: Iridescent. Size of upper petal: Length: Approximately 2.1 cm. Width: 2.7 cm. Size of lateral petals: Length: 2.2 cm. Width: 1.8 cm. Size of lower petals: Length: 2.4 cm. Width: 2.1 cm.

*Flower color.*—Upper surface of petals when fully open: Closest to N155B with blush of 76D, mid-rib of 71D and spot of 71A at base. Lower surface of petals when fully open: Closest to N155B.

*Calyx.*—Quantity of sepals: Three, with the lower sepal modified into a spur. Sepal apex: Acuminate. Sepal texture: Both surfaces are glabrous. Lateral sepal shape: Ovate. Lateral sepal apex: Acuminate. Lateral sepal length: Approximately 1.3 cm. Lateral sepal width: Approximately 0.6 mm. Lateral sepal base: Obtuse. Lateral sepal color: Both surfaces are 144C. Lower sepal shape: Ovate. Lower sepal apex: Acuminate. Lower sepal base: Forms spur. Lower sepal length: Approximately 1.2 cm. Lower sepal width: Approximately 6.9 mm. Lower sepal color of both surfaces: 144B at tip and along mid-line, 155C along margins.

*Spur.*—Quantity: One per flower. Length: Approximately 2.1 cm. Diameter at base: Approximately 1.4 mm. Diameter at tip: Approximately 0.5 mm. Texture: Glabrous. Color: 73D at base gradually transitioning to N144C at tip.

*Peduncle.*—Length: Approximately 2.6 cm. Diameter: Approximately 1.2 mm. Texture: Glabrous. Strength: Strong. Angle to stem: Acute. Color: 145C.

*Reproductive organs.*—Stamen number: 5. Anther shape: Hooded. Anther size: 1.6 mm. Anther color: 8D. Pollen amount: Moderate. Pollen color: 9D. Pistil quantity: 1. Stigma shape: Five pointed star. Stigma length: 0.5 mm. Stigma color: Colorless, transparent. Style length: 1 mm. Style color: 145C. Ovary length: 3 mm. Ovary diameter: 1.5 mm. Ovary texture: Glabrous. Ovary color: N144C.

Seed and fruit development: Neither seed nor fruit production has been observed.

Disease and pest resistance: Resistance to pathogens and pests common to *Impatiens* has not been observed.

What is claimed is:

1. A new and distinct cultivar of *Impatiens* plant named 'Balfafblus', substantially as herein shown and described, which:

1. Exhibits single, very pale violet-colored flowers.
2. Forms dark green-colored foliage.
3. Exhibits a good basal branching character.
4. Exhibits a vigorous, mounded and trailing growth habit.

* * * * *